United States Patent

Hoogeboom et al.

[11] Patent Number: 5,922,007
[45] Date of Patent: Jul. 13, 1999

[54] ENDOSCOPIC SURGICAL INSTRUMENT WITH RATCHET LOCKING DEVICE

[75] Inventors: Thomas J. Hoogeboom, Portage; David L. Richardson, Lawton, both of Mich.

[73] Assignee: Aslan Medical Technologies, Kalamazoo, Mich.

[21] Appl. No.: 09/017,365

[22] Filed: Feb. 2, 1998

[51] Int. Cl.[6] .................................................. A61B 17/00
[52] U.S. Cl. ............................................................ 606/205
[58] Field of Search ...................................... 606/205, 207, 606/107, 206, 170–172, 167; 30/186, 191; 81/418, 421; 604/22

[56] References Cited

U.S. PATENT DOCUMENTS

| | | |
|---|---|---|
| 1,519,938 | 12/1924 | Smith . |
| 1,532,020 | 3/1925 | Angelides . |
| 1,616,121 | 2/1927 | Gruber . |
| 2,137,710 | 11/1938 | Anderson . |
| 2,518,994 | 8/1950 | Miller . |
| 2,989,334 | 6/1961 | Browne . |
| 3,146,015 | 8/1964 | Roberge . |
| 3,265,429 | 8/1966 | Shatt . |
| 4,393,872 | 7/1983 | Reznik et al. . |
| 4,644,651 | 2/1987 | Jacobsen . |
| 4,662,371 | 5/1987 | Whipple et al. . |
| 4,760,848 | 8/1988 | Hasson . |
| 4,872,456 | 10/1989 | Hasson . |
| 4,898,157 | 2/1990 | Messroghli et al. . |
| 4,944,093 | 7/1990 | Falk . |
| 4,944,741 | 7/1990 | Hasson . |
| 5,002,554 | 3/1991 | Korber . |
| 5,009,661 | 4/1991 | Michelson . |
| 5,089,007 | 2/1992 | Kirsch et al. . |
| 5,152,780 | 10/1992 | Honkanen et al. . |
| 5,217,464 | 6/1993 | McDonald . |
| 5,282,817 | 2/1994 | Hoogeboom et al. . |
| 5,470,328 | 11/1995 | Furnish et al. . |
| 5,498,256 | 3/1996 | Furnish . |

FOREIGN PATENT DOCUMENTS

WO8103122 11/1981 WIPO .

*Primary Examiner*—Michael Buiz
*Assistant Examiner*—Vikki Trinh
*Attorney, Agent, or Firm*—Price, Heneveld, Cooper, Dewitt & Litton

[57] ABSTRACT

A surgical instrument includes laterally opposing members, an end effector having opposing jaws movable with respect to each other, a resilient member operably biasing the laterally opposing members away from each other, and an improved ratchet locking device. The ratchet locking device includes a first toothed plate mounted on one of the laterally opposing members, and a second toothed plate pivotally mounted on the other laterally opposing member. The second toothed member is pivotable between a first position in which the plates are engaged and a second position in which the plates are disengaged. A spring member is used for biasing the plates into engagement. A release member is provided for retaining the toothed plates in a disengaged position. The release member is mounted on one of the laterally opposing members and includes a cam surface engagable with a follower on one of the toothed plates. The release member is positionable to selectively retain the toothed plates in an engaged position or in a disengaged position.

8 Claims, 4 Drawing Sheets

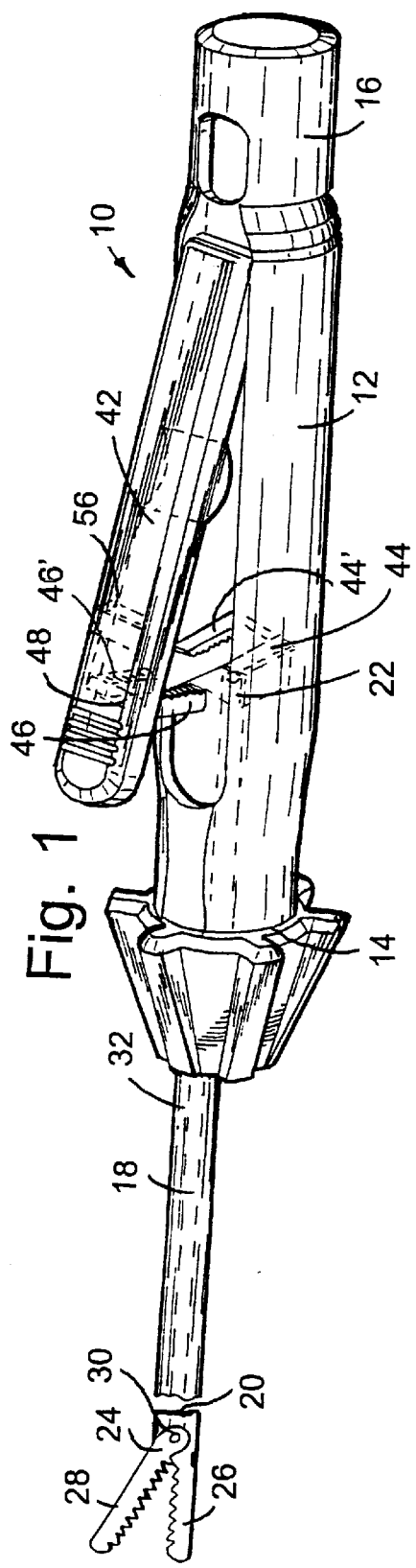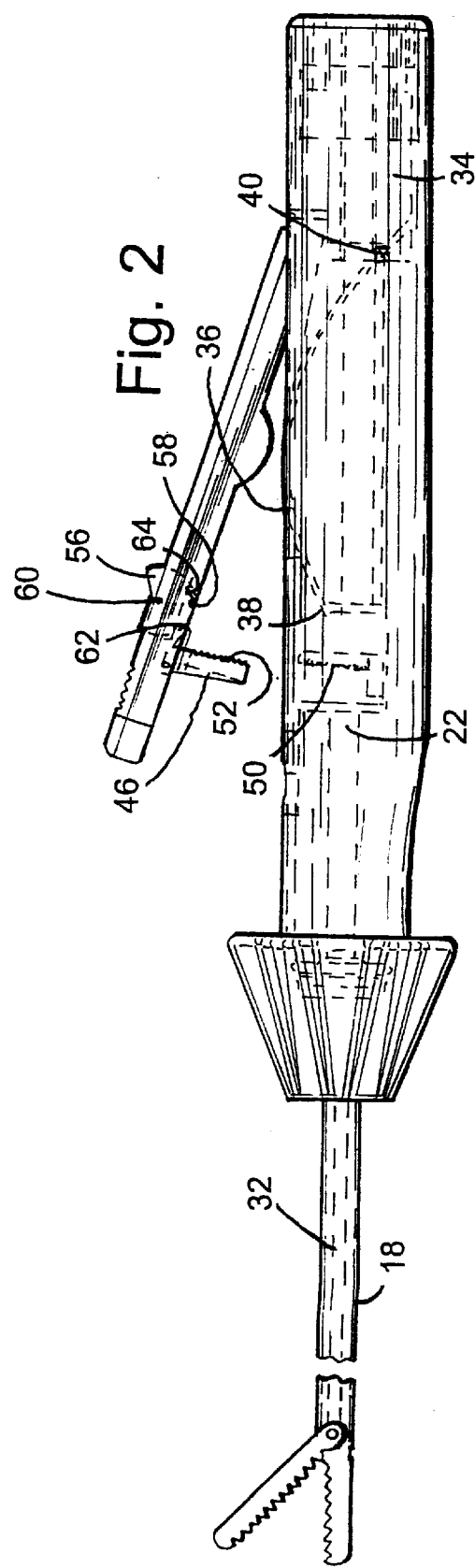

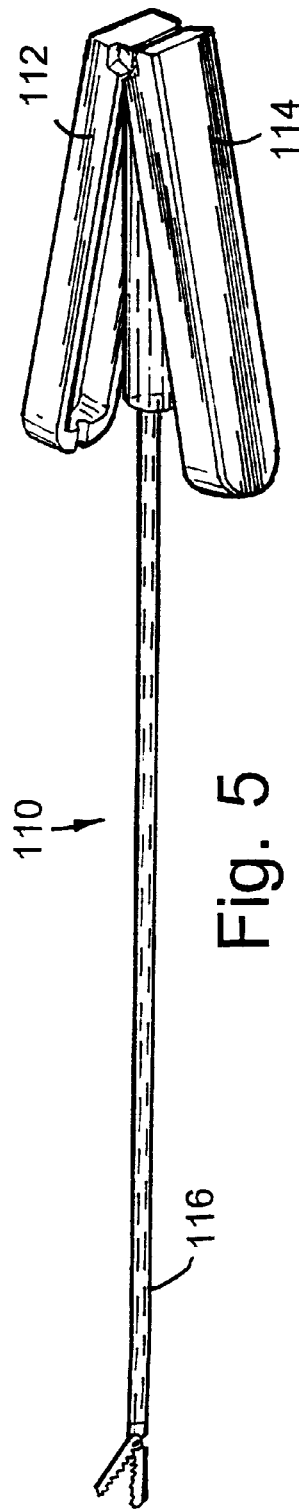
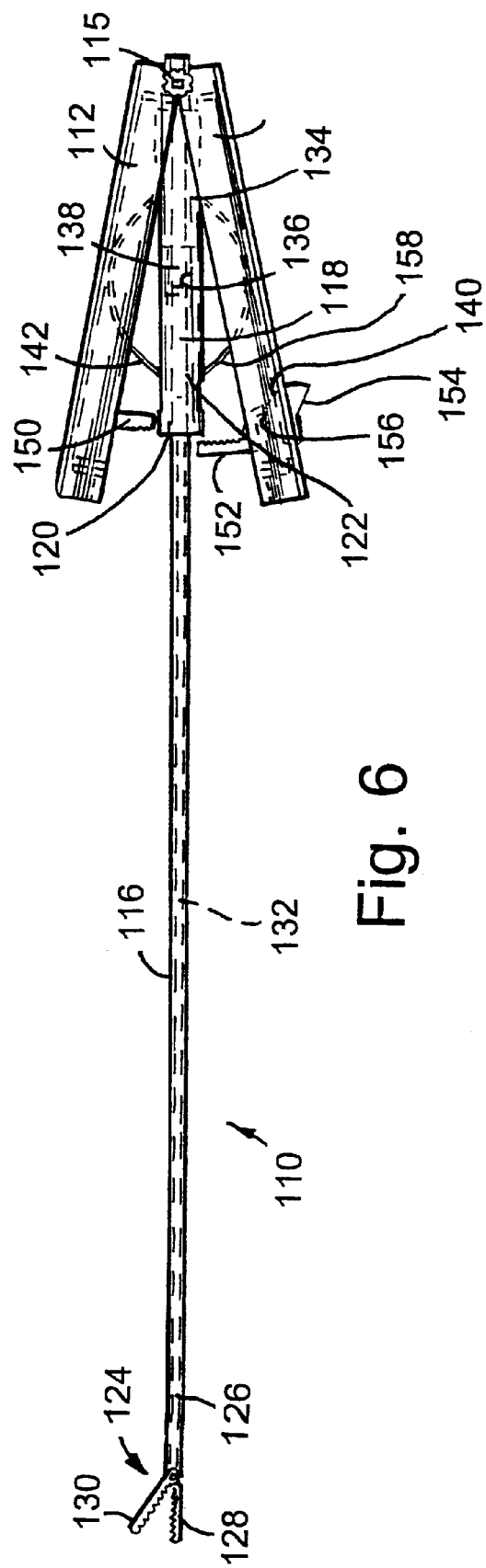

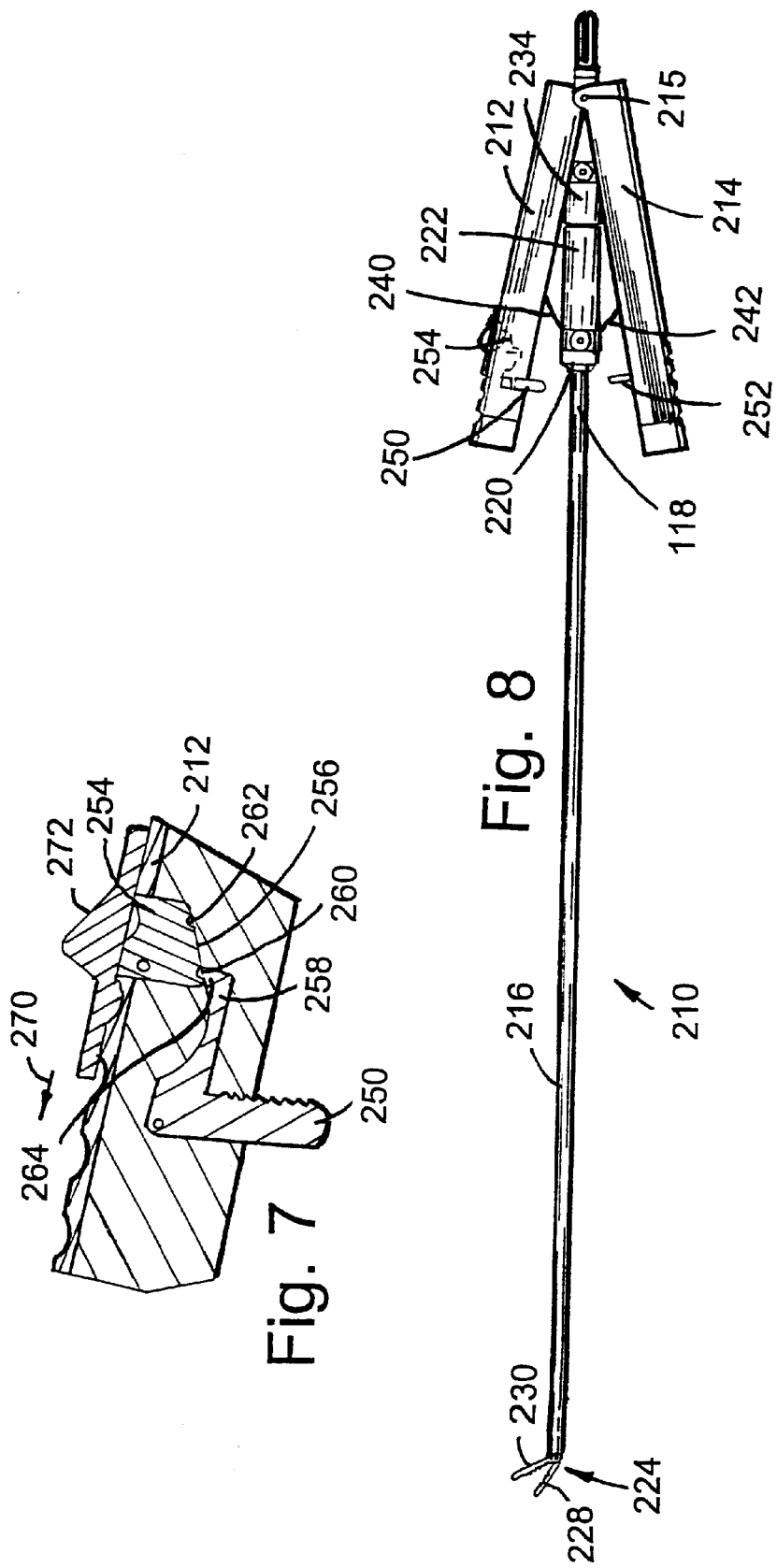

ENDOSCOPIC SURGICAL INSTRUMENT WITH RATCHET LOCKING DEVICE

FIELD OF THE INVENTION

This invention relates generally to the field of surgical instruments for performing cutting, clamping, holding or shearing functions in surgical operations, and more particularly to surgical instruments for performing laparoscopic, endoscopic, and other delicate surgical procedures.

BACKGROUND OF THE INVENTION

My prior U.S. Pat. No. 5,282,817 discloses a surgical instrument which can be easily held in the hand for use in performing delicate surgery. The disclosed instrument is capable of providing enhanced control as compared with other surgical instruments of the same general type. It includes an elongate handle portion including first and second laterally opposing members which are pivotable with respect to each other, an end effector having opposing jaws which are movable with respect to each other, with at least one of the laterally opposing members being operably connected to the movable jaw to effect movement of the opposing jaws with respect to each other when the laterally opposing members are pivoted with respect to each other, and a resilient member operably biasing the laterally opposing members away from each other.

SUMMARY OF THE INVENTION

The present invention comprises such an endoscopic surgical instrument with a locking device for fixing the jaws of the end effector at a desired position with respect to each other. The locking device comprises a first toothed plate mounted on the first laterally opposing member, a second toothed plate pivotally mounted on the second laterally opposing member, a spring member for biasing the second toothed plate into engagement with the first toothed plate, and a release member for retaining the second toothed plate in a position in which it is disengaged from the first toothed plate. The release member includes a cam surface. The second toothed plate includes a follower. The cam surface is engagable with the follower to pivot the second toothed plate away from engagement with the first toothed plate as the release member is pivoted.

BRIEF DESCRIPTION OF THE DRAWINGS

FIG. 1 is a perspective view of a surgical instrument in accordance with one embodiment of the invention;

FIG. 2 is an elevational, cross-sectional view of the instrument shown in FIG. 1;

FIG. 5 is a perspective view of an alternative embodiment of the invention, wherein the ratchet locking device is employed in a surgical instrument having substantially identical laterally opposing members which are pivotable with respect to each other;

FIG. 6 is an elevational view of the surgical instrument shown in FIG. 5;

FIG. 7 is a perspective view of a second alternative embodiment of the invention wherein a ratchet locking device with opposing toothed plates includes a sliding release member having a cam surface engagable with a follower fixed to one of the toothed plates; and FIG. 8 is an enlarged, fragmentary, elevational, cross-sectional view showing details of the ratchet locking device of the instrument shown in FIG. 7.

DESCRIPTION OF THE PREFERRED EMBODIMENTS

Figure 3:
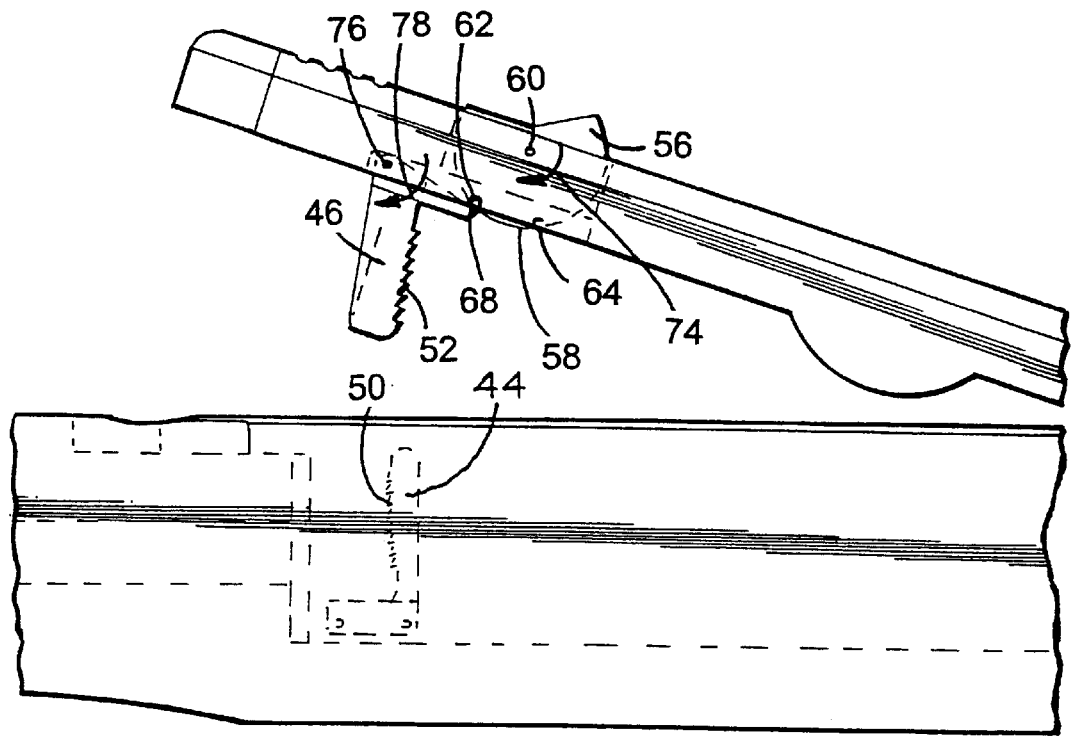
FIG. 3 is an enlarged, fragmentary, elevational, cross-sectional view showing details of the ratchet locking device of the instrument shown in FIGS. 1 and 2 with the lever in the open position.
Figure 4:
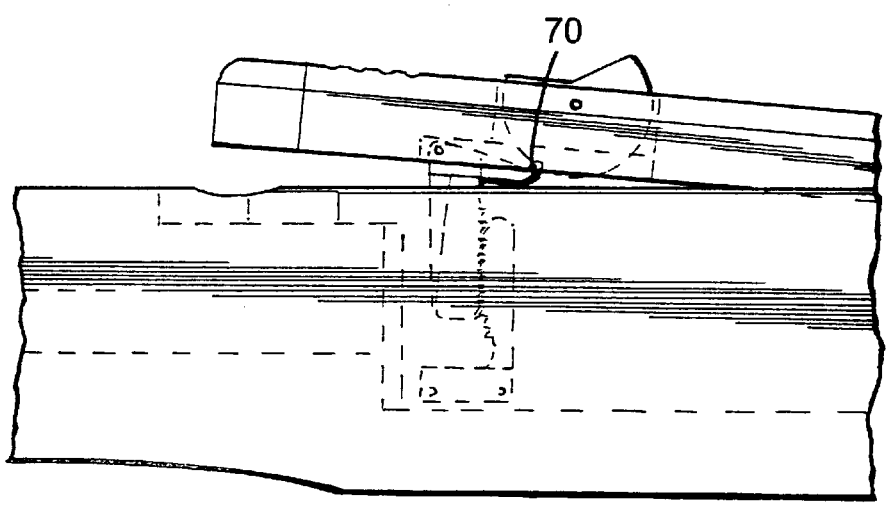
FIG. 4 is an enlarged, fragmentary, elevational, cross-sectional view showing details of the ratchet locking device of the instrument shown in FIGS. 1–3, with the lever in a closed position.

In FIGS. 1 and 2, there is shown a surgical instrument in accordance with a preferred embodiment of the invention. Instrument 10 includes a handle portion generally comprising a handle body 12 having a distal end 14 and a proximal end 16. An elongate tubular member 18 includes a distal end 20 and a proximal end 22. Proximal end 22 of tubular member 18 is fixed to and extends from the distal end 14 of handle body 12. An end effector 24 is located at distal end 20 of tubular member 18. End effector 24 includes opposing jaws 26, 28. In the illustrated embodiment, jaw 26 is fixed, and jaw 28 is movable with respect to jaw 26. More specifically, jaw 28 pivots about pivot axis 30. A linkage rod 32 is slidably positioned in tubular member 18 and is connected at its distal end to movable jaw 28 of end effector 24. Linkage rod 32 extends rearwardly through tubular member 18 and beyond proximal end 22 of tubular member 18. Handle body 12 includes a hollow portion in which a bushing 34 is slidably positioned for reciprocating movement along the longitudinal direction of the handle body. The proximal end of linkage rod 32 is connected to bushing 34.

Surgical instrument 10 includes an improved actuator assembly comprising a resiliently flexible member 36 having a distal end fixed to handle body 12, and a proximal end 40 connected to bushing 34, and a lever 42 pivotally connected to handle body 12. Resiliently flexible member 36 of the illustrated embodiment is a steel leaf spring which is bowed outwardly away from linkage rod 32. Lever 42 is capable of being pivoted toward handle body 12 and contacting resiliently flexible member 36 to cause the resiliently flexible member to be compressed toward linkage rod 32, which in turn causes bushing 34 and linkage rod 32 to move proximally. Proximal movement of linkage rod 32 causes movement of movable jaw 28 of end effector 24.

The ratchet locking device generally comprises a first toothed plate 44 fixed to handle body 12, and a second toothed plate 46 which is pivotally mounted to lever 42. Toothed plate 46 is positioned and normally biased by a spring member 48 into engagement with first toothed plate 44.

Toothed plate 44 and 46 each include a plurality of equally spaced apart teeth which provide a plurality of discrete positions in which the plates can be engaged with each other which correspond with a plurality of discrete positions in which the movable jaw 28 may be positioned with respect to the fixed jaw 26. The teeth of toothed plates 44 and 46 are configured so that the teeth of pivotally mounted toothed plate 46 move and/or snap over the teeth of fixedly mounted toothed plate 44 as pivotally mounted toothed plate 46 is pivoted against the biasing force of spring member 48 when compressive forces are applied to lever 42 and handle body 12 to pivot them toward each other, and so that the teeth of pivotally mounted toothed plate 46 becomes wedged against the teeth of fixedly mounted toothed plate 44 by the biasing force of spring member 48 when compressive forces on the lever and the handle body are removed.

With the illustrated instrument 10, a second toothed plate 44' is fixed to handle body 12, and a second toothed plate 46' is pivotally mounted to lever 42. Plates 44' and 46' engage each other in a manner identical to the manner in which plates 44 and 46 engage each other. Plates 44 and 44' are situated on opposite sides of actuator rod 32. Although a single set of engaging toothed plates (44 and 46) may in some cases be adequate, the position of lever 42 with respect to handle body 12 can be more reliably maintained by providing a pair of engaging toothed plates, one on each side of the linkage rod 32. The toothed surfaces 50 and 52 of toothed plate 44 and 46 respectively, are complimentary arcuate surfaces. In particular, toothed surface 50 is slightly convexed and toothed surface 52 has a complimentary concave surface, the radii of the toothed surfaces 50 and 52 being substantially equal. The arcuate surfaces of toothed plates 44 and 46 provide uniform engagement between the toothed plates along the entire range of discrete positions in which the teeth of the plates 44 and 46 become engaged.

Spring 48 in the illustrated embodiment is a coil spring disposed on a pivot axle fixedly connecting plates 46 and 46'. One end of the coil spring is connected to the pivot axle connecting the plates 46 and 46', and the other end is connected to lever 42 to cause plates 46, 46' to be normally biased into engagement with toothed plates 44 and 44'.

A release member 56 is pivotally mounted on lever 42 and rotates about pivot axis 60. Release member 56 includes an arcuate cam surface 58. Recesses 62 and 64 are defined at opposite ends of arcuate cam surface 58. Toothed plate 46 includes a follower 68 which engages arcuate cam surface 58. Follower 68 includes a pointed projection 70 which stably engages recess 62, whereby toothed plate 46 is retained in a position where it may normally engage toothed plate 44, yet may pivot slightly to allow the teeth of toothed plate 46 to slide past the teeth of toothed plate 44. The distance between pivot axis 60 and recess 64 is greater than the distance between pivot 60 and recess 62, so that as release member 56 is rotated in the direction indicated by arrow 74, the tip 70 of follower 68 is disengaged from recess 62, and cam surface 58, having a gradually increasing radius, causes toothed plate 46 to pivot about pivot axis 76 in the direction indicated by arrow 78, and move out of engagement with toothed plate 44. Eventually, pointed projection 70 of follower 68 snaps into recess 64, whereby toothed plate 46 is stably retained in a position out of engagement with toothed plate 44. In the illustrated embodiment, release member 56 includes recesses 62 and 64 which are engaged by a projection 70 on follower 68. However, as an alternative, release member 56 may be provided with projections at the opposite ends of cam surface 58, and follower 68 may be provided with a recess engaged by projections on opposite ends of cam surface 58.

In operation, release member 56 is pivoted into the position shown in FIG. 3 wherein projection 70 of follower 68 is retained within recess 62, so that toothed plate 46 is held in a position where it will engage toothed plate 44. Lever 42 is then compressed toward handle body 12 causing the teeth on toothed plate 46 to slide over the teeth on toothed plate 44. At the same time, lever 42 engages resiliently flexible member 36 causing it to flatten out and be compressed inwardly toward the linkage rod 32. This causes bushing 34 to move proximally. Rod 32, which is connected to bushing 34, also moves proximally causing movable end effector 28 to move with respect to jaw 26, i.e., closing the jaws of the end effector. When the jaws of the end effector are at a desired position, the compressive force applied between lever 42 and handle body 12 are released, and the end effector and lever are retained at the desired position by engagement of the teeth of toothed plate 46 with those of toothed plate 44. Jaws 26 and 28 can be further tightened as desired by further pivoting lever 42 toward handle body 12. The locking device can be released as desired by rotating the release member 56 in the direction indicated by arrow 74 in FIG. 3, until pointed projection 70 of follower 68 becomes wedged within recess 64. In this position, resiliently flexible member 36 urges lever 42 away from handle body 12, while at the same time urging bushing 34 in a distal direction and returning the movable jaw 28 to the open or starting position.

FIGS. 5 and 6 show an alternative embodiment of the invention wherein the ratchet locking device of the invention is utilized in a surgical instrument 110 including first and second laterally opposing members 112, 114 which are pivotable with respect to each other. In particular, laterally opposing members 112 and 114 are pivotally connected about a pivot axis 115. Instrument 110 also includes an elongate tubular member 116 having a proximal end 118 connected to a distal end 120 of a connector 122. An end effector 124 is located at the distal end 126 of tubular member 116. End effector 124 includes a fixed jaw 128 and a movable jaw 130. A linkage rod 132 is slidably positioned within the tubular member and is connected at its distal end to movable jaw 130. Linkage rod 132 extends rearwardly through tubular member 116, through distal connector 122, and is connected to proximal connector 134. Distal and proximal connectors 122 and 134 are slidably movable with respect to each other along an axis generally coincident with the longitudinal axis of tubular member 116 and linkage rod 132. In particular, in the illustrated embodiment, distal connector 122 includes a cylindrical recess 136, and proximal connector 134 includes a cylindrical projection 138 which is disposed within recess 136 to provide sliding guiding movement of connectors 122 and 134 with respect to each other along the longitudinal axis of the instrument. Laterally opposing leaf spring actuating members 140 and 142 are each attached at one end to connector 122, and at the other end to connector 134. Actuating members 140 and 142 are resiliently flexible members which are normally bowed outwardly as shown in FIGS. 5 and 6. Actuating members 140 and 142 bias laterally opposing members 112 and 114 outwardly away from the longitudinal axis of the instrument as shown in the FIGS. 5 and 6, and also normally bias connectors 122 and 134 into engagement. When opposing members 112 and 114 are laterally compressed toward each other, resiliently flexible members 140 and 142 are also compressed toward each other causing the distal connector 122 to move distally away from the proximal connector 134. This in turn, causes relative movement of linkage rod 132 with respect to tubular member 116, which in turn causes relative movement of jaw 130 with respect to jaw 128. A first toothed plate 150 is mounted to member 112, and a second toothed plate 152 is pivotally mounted to member 114. The second toothed plate is normally biased by a spring member (not shown but substantially identical with spring member 48 of the embodiment shown in FIGS. 1–4) to engage the first toothed plate. The teeth of the toothed plate are configured so that the teeth of the second toothed plate slide over the teeth of the first toothed plate, with the second toothed plate pivoting against the biasing force of the spring member when a compressive force is applied to the laterally opposing members, and so that the teeth of the second toothed plate become wedged against the teeth of the first toothed plate by the biasing force of the spring member when compressive force on the laterally opposing members are removed. A release member 154 is pivotally mounted on member 114. Release member 154 defines an arcuate cam surface 156 for engaging a follower 158 connected to toothed plate 152. The structure and operation of the locking device of instrument 110, comprising toothed plates 150, 152, and release member 154, is substantially the same as the ratchet locking device comprising plates 44 and 46, and release member 56, described with respect to the embodiment shown in FIGS. 1–4 and described above.

The second alternative embodiment of the invention incorporating a sliding release member is shown in FIGS. 7 and 8. Instrument 210 (FIG. 7) includes first and second laterally opposing members 212, 214 which are pivotable with respect to each other. In particular, laterally opposing members 212 and 214 are pivotally connected about a pivot axis 215. Instrument 210 also includes an elongate tubular member 216 having a proximal end 218 connected to a distal end 220 of a connector 222. An end effector 224 includes a fixed jaw 228 and a movable jaw 230. A linkage rod (not shown, but generally similar to linkage rod 132 of instrument 110) is slidably positioned within the tubular member 216 and is connected at its distal end to movable jaw 230. The linkage rod extends rearwardly through tubular member 216, through distal connector 222, and is connected to proximal connector 234. Distal and proximal connectors 222 and 234 are slidably moveable with respect to each other along an axis generally coincident with the longitudinal axis of tubular member 216 and linkage rod 232. In particular, distal connector 222 includes a cylindrical recess (not shown, but generally similar to cylindrical recess 136 of instrument 110), and proximal connector 234 includes a cylindrical projection (not shown, but generally similar to cylindrical projection 138 of instrument 110) which is disposed within the recess to provide sliding guiding movement of connectors 222 and 234 with respect to each other along the longitudinal axis of the instrument. Laterally opposing leaf spring actuating members 240 and 242 are each attached at one end to connector 222, and at the other end to connector 234. Actuating members 240 and 242 are resiliently flexible members which are normally bowed outwardly. Actuating members 240 and 242 bias laterally opposing members 212 and 214 outwardly away from the longitudinal axis of the instrument as shown in FIG. 7, and also normally bias connectors 222 and 234 into engagement. When opposing members 212 and 214 are laterally compressed toward each other, resiliently flexible members 240 and 242 are also compressed toward each other, causing the distal connector 222 to move distally away from the proximal connector 234. This, in turn, causes relative movement of the linkage rod with respect to tubular member 216, which in turn causes relative movement of jaw 230 with respect to jaw 228.

A locking device includes a first toothed plate 250 mounted to member 212, and a second toothed plate 252 pivotally mounted to member 214. The second toothed plate is normally biased by a spring member (not shown, but substantially identical with spring member 48 of the embodiment shown in FIGS. 1–4) to engage the first toothed plate. The teeth of the toothed plate are configured so that the teeth of the second toothed plate slide over the teeth of the first toothed plate, with the second toothed plate pivoting against the biasing force of the spring member when a compressive force is applied to the laterally opposing members, and so that the teeth of the second toothed plate become wedged against the teeth of the first toothed plate by the biasing force of the spring member when compressive force on the laterally opposing members are removed.

Release member 254 (FIG. 8) is slidably mounted on lever 212 for movement along the length thereof. Recesses 260 and 262 are defined at opposite ends of cam surface 256. Follower 258 includes a pointed projection 264 which stably engages recess 260, whereby toothed plate 250 is stably retained in a position out of engagement with toothed plate 252. However, release member 254 can be slid in a distal direction as indicated by arrow 270 by applying pressure, such as with a finger, on surface 272, to cause pointed projection 264 of follower 258 to become disengaged from recess 260, and slide along cam surface 256 until pointed projection 264 engages recess 262. When pointed projection 264 is engaged with recess 262, toothed plate 254 is retained in a position where it may normally engage toothed plate 252, yet may pivot slightly to allow the teeth of toothed plate 250 to slide past the teeth of toothed plate 252. In the illustrated embodiment, release member 254 includes recesses 260 and 262, which are engaged by a projection 264 on follower 258. However, as an alternative, release member 254 may be provided with projections at the opposite ends of cam surface 256, and follower 258 may be provided with a recess engaged by projections on opposite ends of cam surface 256.

In operation, release member 254 may be slid into a position wherein projection 264 of follower 258 is retained within recess 262, so that toothed plate 250 is held in a position where it will engage toothed plate 252. Lever 212 may then be compressed toward lever 214, causing the teeth on toothed plate 250 to slide over the teeth on toothed plate 252. At the same time, levers 212 and 214 engage resiliently flexible members 240 and 242, respectively, causing the resiliently flexible members to flatten out and be compressed inwardly toward the linkage rod. This causes the distal connector 234 to move distally away from the proximal connector 222, which causes relative movement of the linkage rod with respect to tubular member 216, which in turn causes relative movement of jaw 230 with respect to jaw 228. When the jaws of the end defector are at a desired position, the compressive force applied between levers 212 and 214 are released, and the end defector and levers are retained at the desired position by engagement of teeth of toothed plate 250 with those of toothed plate 252. Jaws 228 and 230 can be further tightened as desired by further pivoting levers 112 and 114 toward each other. The locking device can be released as desired by sliding release member 254 distally until pointed projection 264 again engages recess 260 as shown in FIG. 8.

It will be understood that the invention may be embodied in other specific forms without departing from the spirit or central characteristics thereof. The present examples and embodiments, therefore, are to be considered in all respects as illustrated and not restrictive, and the invention is not limited to the details given herein and should be understood as defined by the following claims.

What is claimed is:

1. A surgical instrument comprising:
   first and second laterally opposing members which are pivotable with respect to each other;
   an end effector having opposing jaws, at least one of which is movable with respect to the other, at least one of the laterally opposing members being operably connected to the movable jaw to effect movement of the opposing jaws with respect to each other when the laterally opposing members are pivoted with respect to each other;
   a resilient member operably biasing the laterally opposing members away from each other;

a first toothed plate mounted on the first laterally opposing member;

a second toothed plate pivotally mounted on the second laterally opposing member, the second toothed plate being pivotable between a first position in which the teeth of the toothed plates are engaged and a second position in which the second toothed plate is pivoted away from engagement with the first toothed plate;

a spring biasing the second toothed plate into engagement with the first toothed plate; and a release member for retaining the second toothed plate in the second position in which the toothed plates are disengaged, the release member being mounted on one of the laterally opposing members and including a cam surface, the second toothed plate including a follower, the cam surface being engagable with the follower to pivot the second toothed plate away from engagement with the first tooth plate as the release member is pivoted.

2. The surgical instrument of claim 1, wherein the toothed plates have complimentary arcuate toothed surfaces.

3. The surgical instrument of claim 1, wherein the release member is pivotally mounted on one of the laterally opposing members.

4. The surgical instrument of claim 1, wherein the release member is slidably mounted on one of the laterally opposing members.

5. A surgical instrument comprising:

a handle portion including first and second laterally opposing members which are pivotable with respect to each other;

an elongate tubular member having a distal end and a proximal end, the tubular member being attached to a distal end of the handle portion;

an end effector at the distal end of the tubular member, the end effector including opposing jaws, at least one of the jaws being movable with respect to the other;

a linkage rod having a distal end and a proximal end, the linkage rod slidably positioned in the tubular member and connected at its distal end to the movable jaw of the end effector, the linkage rod extending rearwardly from the tubular member and beyond the proximal end of the tubular member;

at least one of the laterally opposing members being operably connected to the proximal end of the linkage rod, whereby pivoting of the laterally opposing members with respect to each other causes movement of the linkage rod and thereby effects movement of the jaws of the end effector with respect to each other;

a resilient member operably biasing the laterally opposing members away from each other;

a first toothed plate mounted to the first of the laterally opposing members;

a second toothed plate pivotally mounted to the second of the laterally opposing members, the second toothed plate being normally biased by a spring member to engage the first toothed plate;

the teeth of the toothed plate being configured so that the teeth of the second toothed plate move over the teeth of the first toothed plate, with the second toothed plate pivoting against the biasing force of the spring member when a compressive force is applied to the laterally opposing members, and so that the teeth of the second toothed plate become wedged against the teeth of the first toothed plate by the biasing force of the spring member when compressive forces on the laterally opposing members are removed; and a release member mounted to one of the laterally opposing members, the release member defining a cam surface and a projection or a recess at first and second ends of the cam surface, the second toothed plate including a follower engagable with the cam surface, the follower including a recess or a projection which is engagable with the projection or recess at each end of the cam surface to selectively retain the follower at one of the first and second ends of the cam surface, the release member being movable between a first position wherein the follower is retained at the first end of the cam surface and wherein the teeth of the second toothed plate engage the teeth of the first toothed plate, and a second position wherein the follower is retained at the second end of the cam surface and wherein the second toothed plate is pivoted away from engagement with the first toothed plate by the release member whereby the laterally opposing members are urged away from each other by the resilient member.

6. The surgical instrument of claim 3, wherein the toothed plates have complimentary arcuate toothed surfaces.

7. The surgical instrument of claim 5, wherein the release member is pivotally mounted on one of the laterally opposing members.

8. The surgical instrument of claim 5, wherein the release member is slidably mounted on one of the laterally opposing members.

* * * * *

UNITED STATES PATENT AND TRADEMARK OFFICE
CERTIFICATE OF CORRECTION

PATENT NO. : 5,922,007
DATED : July 13, 1999
INVENTOR(S) : HOOGEBOOM ET AL.

It is certified that error appears in the above-identified patent and that said Letters Patent is hereby corrected as shown below:

Column 3, Lines 12 & 14;
 "complimentary" should be --complementary--.

Column 7, Claim 2, Line 22;
 "complimentary" should be --complementary--.

Column 8, Claim 6, Line 41;
 "complimentary" should be --complementary--.

Signed and Sealed this

Twenty-second Day of May, 2001

Attest:

NICHOLAS P. GODICI

Attesting Officer          Acting Director of the United States Patent and Trademark Office